(12) United States Patent
Mathes et al.

(10) Patent No.: US 6,461,860 B2
(45) Date of Patent: Oct. 8, 2002

(54) ALIGNMENT MECHANISM FOR TWO-ELECTRODE VOLTAGE-CLAMP PERFUSION CHAMBER FOR ELECTROPHYSIOLOGICAL TESTING OF OOCYTES

(75) Inventors: Christopher W. Mathes, Union City, CA (US); Gregory A. Hamersly, Atascadero, CA (US)

(73) Assignee: Axon Instruments, Inc., Union City, CA (US)

( * ) Notice: Subject to any disclaimer, the term of this patent is extended or adjusted under 35 U.S.C. 154(b) by 62 days.

(21) Appl. No.: 09/769,609

(22) Filed: Jan. 25, 2001

(65) Prior Publication Data

US 2002/0098575 A1 Jul. 25, 2002

(51) Int. Cl.$^7$ ................................................. C12M 3/00
(52) U.S. Cl. ..................... 435/286.7; 435/29; 435/32; 435/287.3; 435/307.1
(58) Field of Search ............................. 435/4, 29, 30, 435/1.1, 1.2, 32, 33, 285.2, 286.1, 286.2, 286.4, 287.1, 287.3, 288.3, 288.7, 307.1; 359/395, 398; 436/63

(56) References Cited

U.S. PATENT DOCUMENTS 4,270,838 A * 6/1981 Furusawa et al. ........... 359/385

| 4,920,053 A | * | 4/1990 | Inoue et al. | 359/368 |
| 6,268,121 B1 | * | 7/2001 | Takeshita et al. | 204/400 |
| 6,358,749 B1 | * | 3/2002 | Orthman | 359/368 |

FOREIGN PATENT DOCUMENTS

| GB | 1 501 253 | * | 2/1978 |
| JP | 09-196936 A | * | 7/1997 |
| WO | WO098/50791 A1 | * | 11/1998 |

* cited by examiner

Primary Examiner—William H. Beisner
(74) Attorney, Agent, or Firm—Antonio R. Durando; Durando Birdwell & Janke, PLC

(57) ABSTRACT

An automated mechanism for guiding a microelectrode toward an oocyte placed in a perfusion chamber consists of a movable guide tube holding the electrode and a fixed guide collar in fixed relation to the target oocyte. Because the guide tube and guide collar are independently mounted, the alignment of the tip of the microelectrode is effected by its placement within the precisely aligned guide collar, irrespective of any fine misalignment of the guide tube. Accordingly, a change of microelectrode in the guide tube does not affect its final alignment toward the oocyte so long as the calibration of the guide collar is not disturbed, thereby providing a mechanism for maintaining the alignment of different microelectrodes successively mounted in the system without requiring recalibration.

45 Claims, 12 Drawing Sheets

ALIGNMENT MECHANISM FOR TWO-ELECTRODE VOLTAGE-CLAMP PERFUSION CHAMBER FOR ELECTROPHYSIOLOGICAL TESTING OF OOCYTES

BACKGROUND OF THE INVENTION

1. Field of the Invention

This invention is related in general to apparatus for aligning the microelectrodes of a voltage-clamp perfusion chamber with a target oocyte and, in particular, to an alignment mechanism suitable for automated, repeatable implementation while measuring in parallel electrophysiological responses from multiple frog oocytes in sequential experiments.

2. Description of the Related Art

As detailed in commonly-owned copending application Ser. No. 09/586,633, herein incorporated by reference in its entirety, the normal process of drug discovery involves a number of distinct stages from the initial identification of a potentially useful substance to the final step of clinical testing. Multiple screening steps are necessary to isolate substances of interest from libraries of potentially useful compounds.

The explosion of data made available from genetic research coupled with advances in chemical synthesis has produced a great demand for ever-higher screening rates to test potentially therapeutic compounds. Thus, the ability to screen compound libraries at higher and higher throughput is becoming increasingly critical in the search for new drugs, which is now a large-scale industrial activity. Accordingly, there is a growing need for integrated laboratory systems that assess large numbers of compounds quickly.

Of particular relevance to the present invention are assays conducted on Xenopus frog oocytes, which are uniquely suitable for screening of ion channels linked to a variety of diseases. Using conventional voltage clamping across the membrane of the oocyte, the voltage dependence of ion channel activity in the oocyte cell is assessed by measuring current changes produced in response to exposure to multiple test solutions. Testing of an oocyte cell under voltage-clamped conditions, a technique that is well known in the art, is carried out in batch operations in a chamber designed to support an individual oocyte being perfused with a test solution. The cell membrane is pierced with two microelectrodes of a voltage-clamp amplifier capable of recording current variations in response to voltage step changes or to the application of compounds under constant-voltage conditions.

A conventional two-electrode voltage-clamp system 10 is illustrated schematically in FIG. 1, where numerals 12 and 14 refer to a voltage-recording microelectrode and a current-passing microelectrode, respectively, inserted through the membrane 16 of an oocyte cell C. The membrane potential $V_m$ is recorded by a unit-gain buffer amplifier 18 connected to the microelectrode 12. The membrane potential $V_m$ is compared to a control potential $V_c$ in a high-gain differential amplifier 20 (with gain $\mu$) producing a voltage output $V_\epsilon$ proportional to the difference $\epsilon$ between $V_m$ and $V_c$. The voltage $V_\epsilon$ at the output of the differential amplifier 20 forces current to flow through the current-passing microelectrode 14 into the oocyte cell C, such as to drive the error $\epsilon$ to zero and maintain the membrane voltage clamped at $V_c$. The circuit is completed through a ground 22 across the cell membrane, which in the schematic drawing is modeled by impedance and capacitance values $R_m$ and $C_m$, respectively.

One of the main concerns in designing perfusion chambers for oocytes is the ability to isolate the oocyte cell in a stationary condition, so that it can be contacted by the voltage-clamp microelectrodes and exposed to the test solution of interest. U.S. Ser. No. 09/586,633 describes a perfusion chamber design characterized by a porous oocyte support structure with a sloped top surface that produces the automatic entrapment of the underside of the oocyte, thereby localizing the cell in a predetermined fixed position within the reach of dedicated voltage-clamp microelectrodes. The test solution is delivered continuously at the top of the chamber, above the oocyte, and withdrawn from the bottom of the chamber, below the oocyte. The porosity of the support material enables the continuous perfusion of test solution around the membrane of the oocyte, including its bottom portion that is firmly in place within the holding well. The geometry of the holding well is judiciously selected, as a function of the specific oocyte or other cell being tested, to ensure the automatic and precise placement of the cell by gravity and to optimize the pressure distribution over its membrane, thereby minimizing the probability of rupture or other damage to the cell. Once so restrained, the test cell is connected to the voltage-clamp microelectrodes and perfused with test solution in a batch operation.

The ooycyte cells C under investigation and the microelectrodes 12,14 of voltage-clamp apparatus are extremely small (typically about 1.0 mm to 1.5 mm in diameter, with the electrodes coming to a point about 0.12 mm wide). Therefore, the process of alignment of the oocyte positioned in the well of the perfusion chamber with the microelectrodes of the voltage-clamp apparatus involves a precise operation and is typically carried out by an operator with the aid of a microscope and a micromanipulator in individual workstations, performing one experiment at a time. Accordingly, it is not suitable for automated, higher-throughput, parallel-testing applications. Moreover, the configuration of many prior-art chambers often impedes direct access of the microelectrodes to the oocyte, thereby further complicating automatic insertion of the electrodes. Japanese Patent Bulletin No. 11-299496 (Fukusono et al.) describes a family of oocyte perfusion devices developed to solve this alignment problem in single-electrode voltage-clamp environments. The oocyte is placed in a conical chamber at the bottom of a cylindrical passage adapted for aligning the microelectrode with the oocyte. Because of the perfect alignment between the oocyte fixed to the chamber and the microelectrode, the tip of the electrode can be easily inserted into the oocyte without the aid of a microscope or micromanipulator. The insertion of the microelectrode can be effected manually or through a variety of mechanisms producing the linear motion of the electrode. Thus, the oocyte chamber serves the dual purpose of housing the oocyte and guiding a single microelectrode toward the oocyte.

While useful for facilitating the alignment of the microelectrode with the oocyte, the concept described by Fukusono et al. is not suitable for two-electrode voltage-clamp applications. Furthermore, it does not provide for the mechanical engagement and disengagement of the electrode from the alignment passage, which is critical for automated operation. Accordingly, the disclosed devices as well as other prior-art apparatus are not well suited for the high-throughput, electronically manipulated, automated-system needs of today's pharmaceutical industry. This invention provides a mechanism designed to address these needs.

BRIEF SUMMARY OF THE INVENTION

The primary objective of this invention is a voltage-clamp apparatus suitable for sequential testing of animal cells through successive exposures to multiple perfusion solutions in an automated, continuous system.

In particular, an objective of the invention is an automated alignment system for the correct placement of the voltage-clamp electrodes within the perfusion chamber, so that no microscope or other manually operated control device is used to guide the electrodes into the test cell.

A goal is also a microelectrode alignment system that permits the rapid change of an inoperative electrode without the need for recalibration of the guiding mechanism.

Another goal of the invention is a design particularly suitable for the testing of oocytes, especially *Xenopus* oocytes.

Another objective is a voltage-clamp apparatus that can be adapted for parallel testing of multiple oocytes in a higher-throughput testing system.

Another goal is a voltage-clamp design that is suitable for implementation within an overall automated voltage-clamp and solution-delivery system.

Yet another object is a system that can be implemented using conventional voltage-clamp hardware and software, modified only to the extent necessary to meet the design parameters of the chamber and the microelectrode alignment system of the invention.

Still another goal is a method of perfusion that enables the rapid, sequential testing of multiple oocytes with multiple test solutions on a continuous sequential basis.

A final objective is a system that can be implemented economically according to the above stated criteria.

Therefore, according to these and other objectives, the present invention consists of an automated mechanism for guiding a microelectrode toward an oocyte placed in a perfusion chamber in substantial alignment with a predetermined angle of attack deemed optimal for penetrating the oocyte. According to one aspect of the invention, the final fine alignment of the microelectrode is achieved by precisely fitting the cylindrical portion of the electrode into a conforming guide collar disposed in fixed alignment with the intended direction for voltage-clamp electrode operation. The microelectrode is loosely mounted into a guide tube that is independent of the guide collar and is adapted for advancing the electrode through the guide collar to the desired position in contact with the oocyte for testing purposes, and for retrieving the electrode out of the guide collar for replacement purposes. Because the guide tube and guide collar are independently mounted, the alignment of the tip of the microelectrode is effected by its placement within the precisely aligned guide collar, irrespective of any fine misalignments in the guide tube. Accordingly, a change of microelectrode in the guide tube does not affect its final alignment in the oocyte so long as the calibration of the guide collar is not disturbed, thereby providing a mechanism for maintaining the alignment of successive microelectrodes mounted in the system without the need for recalibration.

According to another aspect of the invention, the advancement of the tip of the microelectrode into the oocyte is controlled by tracking the impedance and/or voltage measured by the electrode as it advances through the perfusion chamber. Measurable changes occur when the tip of the electrode contacts the perfusion solution and then again when it touches and penetrates the membrane of the oocyte sample, thereby providing control signals suitable for the automated positioning of the microelectrode. According to still another aspect of the invention, a "vibration" (in the form of a mechanical oscillation or an electrical buzz) may be introduced in the tip of the microelectrode as it advances toward the membrane of the oocyte in order to facilitate its penetration and avoid dimpling that may cause rupture of the cell.

Because the apparatus of the invention can operate fully on an automated basis, it is suitable for use in multi-chamber parallel-testing systems wherein each chamber is used sequentially to test series of oocytes with a variety of perfusion solutions. Multiple perfusion chambers equipped with the electrode alignment mechanism of the invention can be operated independently and in parallel with greatly reduced manual operation. In essence, operator intervention is only required for changing oocytes and for maintenance, such as replacing microelectrodes periodically or after they are damaged, and for controlling the schedule of testing. By using modular components for the perfusion chamber, the guide collar structure and the guide tube structure, perfusion chambers and/or microelectrodes can be changed between tests without the need for recalibration of the electrode alignment. Therefore, series of successive tests can be carried out rapidly and precisely.

Various other purposes and advantages of the invention will become clear from its description in the specification that follows and from the novel features particularly pointed out in the appended claims. Therefore, to the accomplishment of the objectives described above, this invention consists of the features hereinafter illustrated in the drawings, fully described in the detailed description of the preferred embodiment and particularly pointed out in the claims. However, such drawings and description disclose but one of the various ways in which the invention may be practiced.

DESCRIPTION OF THE PREFERRED EMBODIMENTS OF THE INVENTION

The heart of this invention lies in the idea of combining two independent components in an alignment mechanism for properly placing a voltage-clamp electrode within a test oocyte. The first component consists of a structure for removably mounting a microelectrode in coarse-alignment position for advancement toward the oocyte held in a perfusion chamber. The second component consists of a structure disposed in fixed spatial relation to the perfusion chamber and adapted to receive the tip of the microelectrode and finely align it with the oocyte. Other inventive aspects lie in the specific design used to implement the concept of the invention in a versatile, automated, efficient system.

Figure 1:
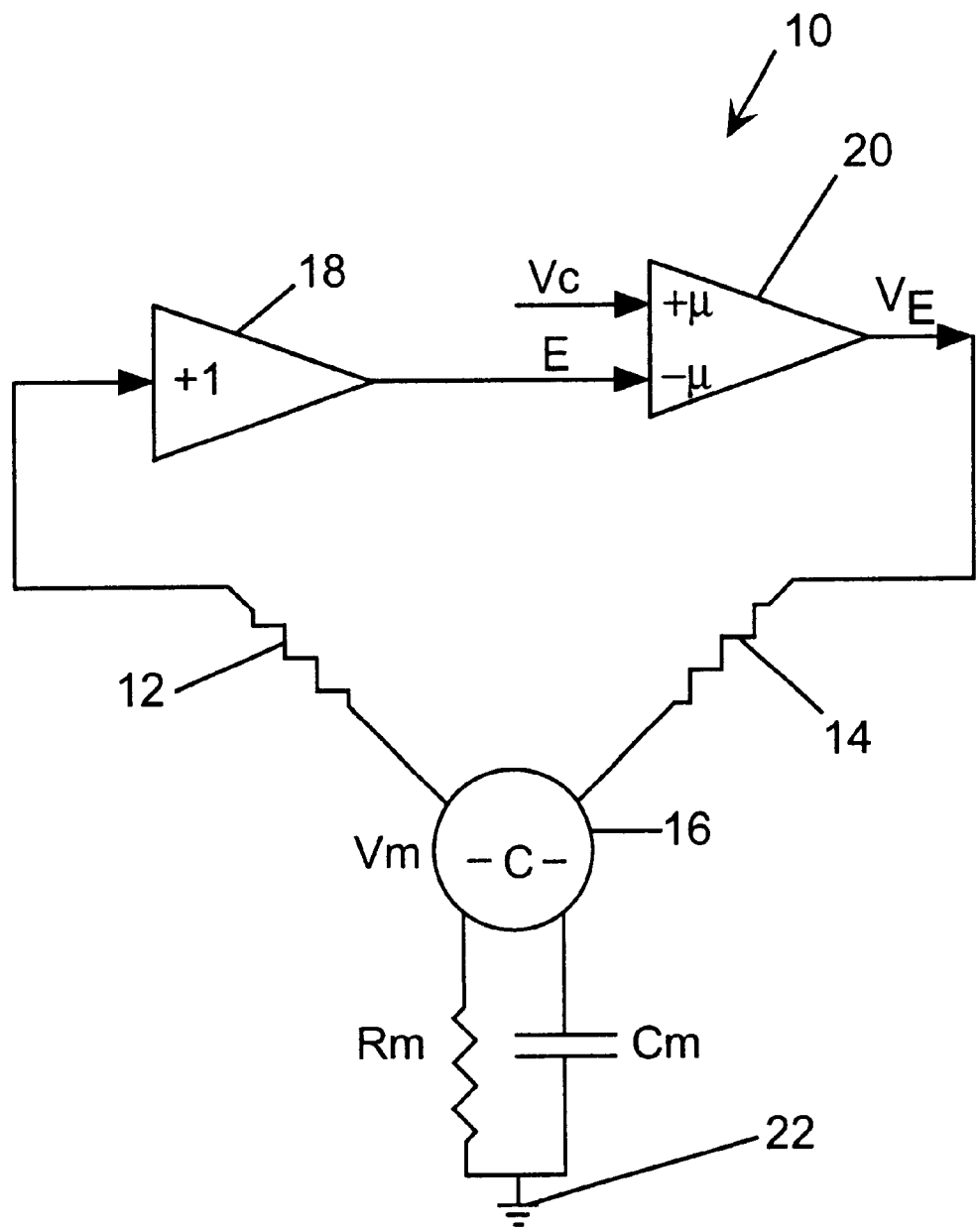
FIG. 1 is a schematic diagram of a conventional two-electrode voltage-clamp circuit applied to a cell in a test chamber.
Figure 2:
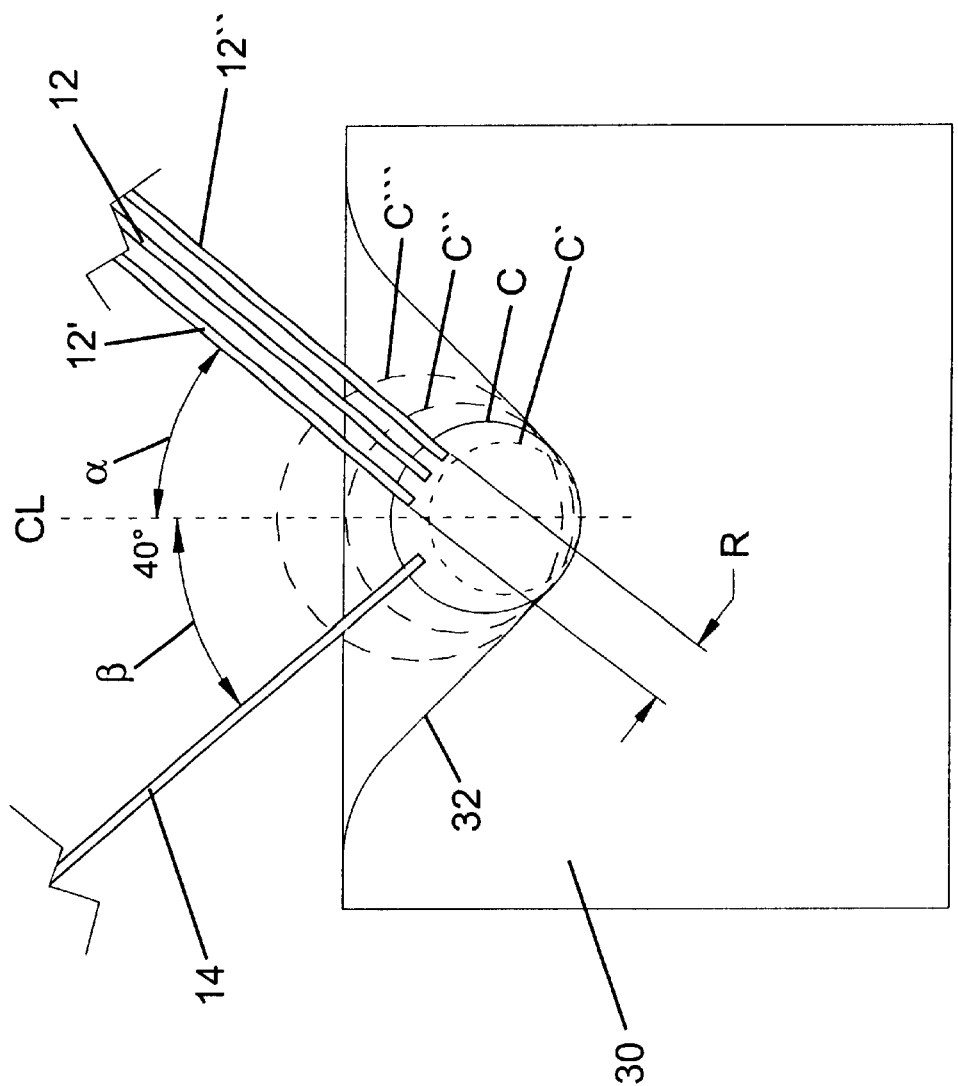
FIG. 2 is a schematic, cross-sectional, elevational view of a perfusion-chamber support structure suitable for the invention showing an oocyte cell secured in position in a test well for connection with voltage-clamp microelectrodes.

Referring to the figures, wherein the same reference numerals and symbols are used throughout for like parts, FIG. 2 is a sectioned schematic illustration of the perfusion chamber disclosed in Ser. No. 09/586,633, which is particularly suitable for the alignment mechanism of the invention because it provides relatively clear access to a firmly positioned oocyte. The drawing shows a porous support structure 30 in a vertical section through the center of a holding well 32 sized for retaining an oocyte cell C of average size. The well 32 consists of a crater with perfectly round horizontal cross-sections of gradually decreasing diameter toward a centered bottom. Similarly, the rest of the support structure 30 has a sloped top surface progressively converging downward toward the holding well.

Thus, the convergence of each side of the support structure 30 toward the central bottom of the crater produces the automatic gravitational placement of the oocyte in a predetermined assured position that permits the repetitive and consistent placement of voltage-clamp microelectrodes 12,14 into the oocyte. In order to minimize the probability of damage to the oocyte's membrane after placement within the well 32, the geometry of the bottom portion of the well is also designed so as to distribute the pressure exerted on the membrane as evenly as possible. The contour of the well is shaped to envelop the natural profile of the cell, which, in the case of an oocyte, tends to be substantially spherical. Since a different profile would be required to fit cells of different sizes, a geometry for an average cell size is preferably selected. For *Xenopus oocytes,* the most frequently used cells for certain types of target screening, the preferred geometry of the bottom portion of the well 30 is chosen to conform to the surface of a sphere with a diameter of about 1.0 mm, as illustrated in the figure. These features have been found to provide great stability to the oocyte for the purpose of voltage clamping and perfusion.

As illustrated in FIG. 2, the ideal position for the microelectrodes 12 and 14 is to be aligned at some angles α and β (which may be the same), respectively, with the center of the oocyte cell C, so that penetration through the cell membrane is substantially perpendicular to the surface of the cell. This minimizes the probability of cell displacement or damage, which may occur when the direction of penetration has a tangential component. For example, if the microelectrode 12 were positioned off center, as illustrated in phantom line by electrodes 12' and 12", the oocyte C would have the tendency to roll counterclockwise and clockwise, respectively, with a greater probability to cause damage to the cell. Accordingly, for automated operation it is necessary to define a range of microelectrode positions considered acceptable for the variety of oocyte sizes being tested. For example, a tolerance R of 0.36 mm (±0.18 mm from the desired alignment position) was found to be optimal for *Xenopus oocytes,* as shown in the figure. Therefore, this tolerance was used in developing the apparatus of the invention. FIG. 2 illustrates the relative alignment of the electrode 12 with different-size oocytes C', C, C" and C"' with diameters of 0.8, 1.0, 1.2 and 1.5 millimeters, respectively.

Figure 3:
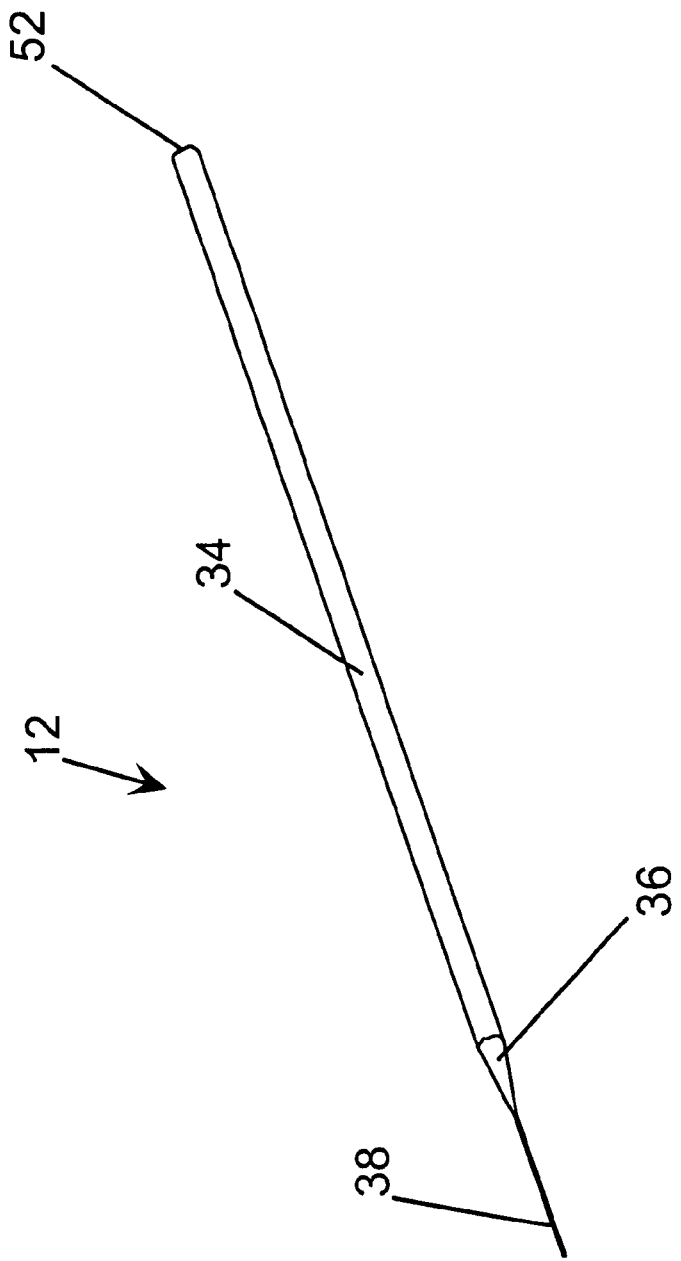
FIG. 3 is a plan view of a conventional microelectrode, as used with the alignment apparatus of the invention.

Conventional microelectrodes consist of glass tubes with a concentric tip formed by heating and pulling one end concentrically to a point, as illustrated in FIG. 3. A typical microelectrode 12 (or 14) is about 80 mm long and consists of a main cylindrical section 34, a frustoconical section 36 and a tip section 38. The main section 34 is about 65 to 70 mm long and has an outside diameter of about 1.5 mm; the frustoconical section is about 5 mm long; and the tip section is about 5–10 mm long with a maximum outside diameter of 0.12 mm. The microelectrode is filled with an electrolytic solution and the tip is perforated, so that the liquid inside the electrode is in fluid communication with the liquid in which the electrode is immersed.

Figure 4:
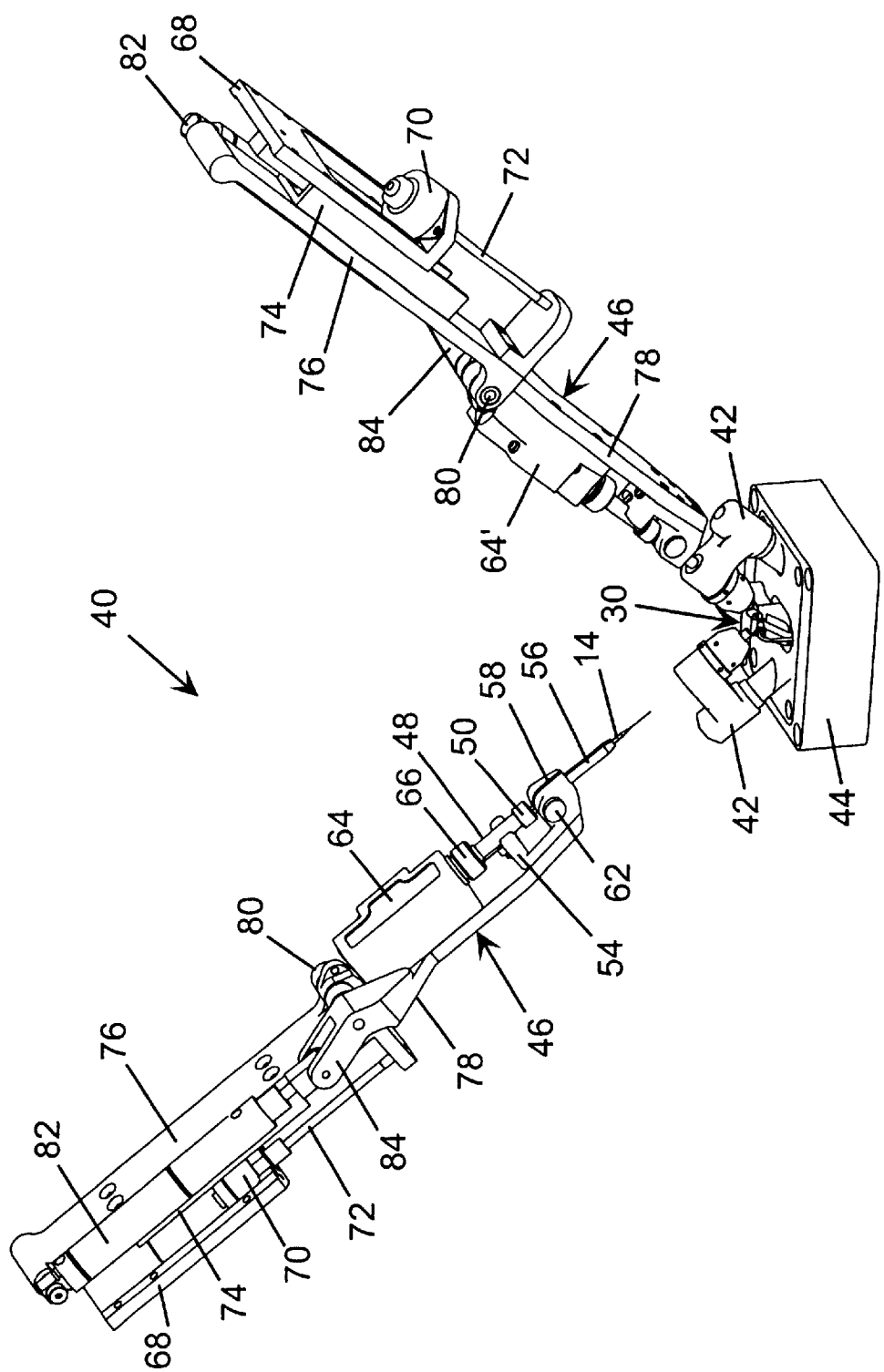
FIG. 4 is a partially sectioned and exploded, perspective view of the alignment apparatus of the invention installed over the perfusion chamber of FIG. 2; the drawing also shows inlet and outlet plumbing and an aspirator to remove excess liquid in the chamber.

The alignment apparatus 40 of the invention is shown in FIG. 4 in partially sectioned, perspective view, with reference to the perfusion chamber and the microelectrodes illustrated in FIGS. 2 and 3. The invention is described mostly with reference to the disengaged components shown on the left of the figure, corresponding to the current-passing microelectrode 14, but it is understood that the coupled components on the right, corresponding to the voltage-recording microelectrode 12, comprise equivalent structure. A first, stationary component consists of a guide head 42 that is rigidly attached to one side of a rigid frame 44 containing the support structure 30 of the perfusion chamber (more clearly illustrated in the enlarged views of FIGS. 5A and 5B), so as to maintain a fixed alignment position between the guide head 42 and the well 32 of the chamber. A second, movable component consists of an electrode stage 46 that is adapted for housing and advancing (or retracting) the microelectrode 14 in substantial alignment with the guide head 42 toward the center of the oocyte cell C placed in the perfusion chamber.

A tubular electrode holder 48 with a tightening friction nut 50 is provided to mount the microelectrode 14 in the stage 46. The electrode 14 is held in place by placing its proximal end 52 (FIG. 3) inside the holder 48 and tightening the nut 50 to frictionally engage and retain the electrode. The holder 48 is rigidly attached to a stage nose 54 that includes a guide tube 56 projecting downward toward the guide head 42 in alignment with the oocyte in the perfusion chamber. As seen more clearly in the view of FIG. 6, both the stage nose 54 and the guide tube 56 have longitudinal slots 58 and 60, respectively, that make it possible to insert or extract the microelectrode 14 directly into or from the nut 50 and the holder 48 without threading it through the guide tube, thereby facilitating the process of installation and removal of the electrode. A releasable lock mechanism 62 is preferably also provided to center and securely lock in place the microelectrode 14 within the guide tube 56 to complete the process of installation. The electrode holder 48 and the microelectrode 14 are electrically coupled to an electronic module 64 through a connector 66 to provide the conventional current-passing function described above. (A similar electronic module 64' provides the voltage-recording function required for the microelectrode 12 shown on the right side of FIG. 4.) The electrode stage 46 is rigidly mounted by means of a support flange 68 on a fixed frame 114 (seen in FIG. 9) that enables the reliable coarse alignment of the guide tube 56 and the microelectrode 14 mounted within it with the target oocyte in the perfusion chamber. The flange 68 provides a fixed reference in relation to which the stage nose 54 can be moved to advance the microelectrode 14 toward the oocyte C, to retract the microelectrode from the oocyte, or to rotate the stage nose to facilitate the replacement of the microelectrode. Accordingly, a linear actuator, such as a stepper motor 70 with a fine-pitch screw drive 72, and a linear slide 74, acting between the support flange 68 and the electrode stage 46, are used to advance or retract the microelectrode 14 in alignment with the oocyte C in the perfusion chamber. (The right side of FIG. 4 illustrates the electrode stage 46 advanced through the guide head 42 toward the oocyte cell C.) Finally, in order to facilitate the removal and installation of the microelectrode, the electrode stage 46 includes two separate plates 76,78 pivotally connected through a conventional hinge 80. A hydraulic ram 82 (or, equivalently, a stepper motor) acting on a lever arm 84 makes it possible to rotate upward, away from the perfusion chamber, the plate 78 and the stage nose 54 affixed to it, thereby providing rapid and easy access to the microelectrode.

Figure 5A:
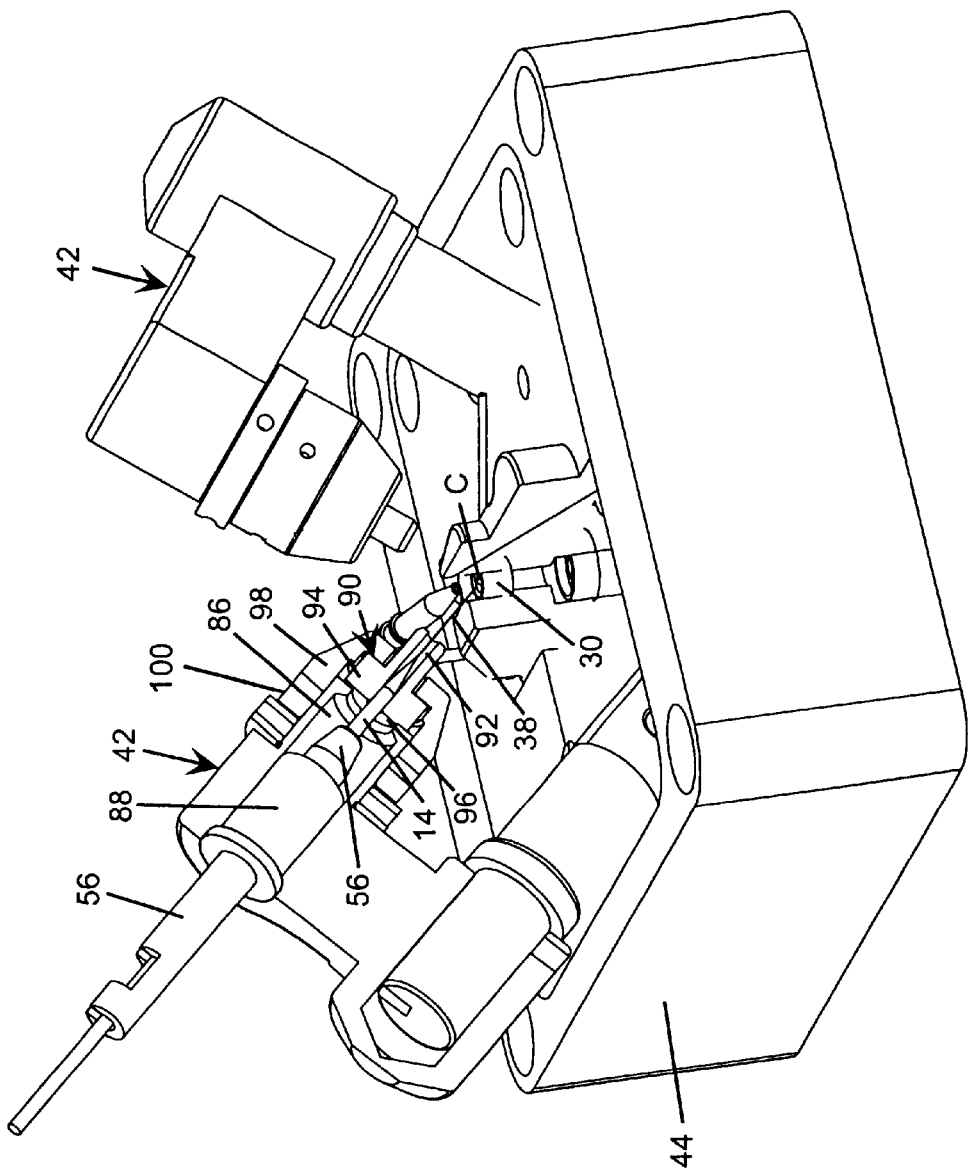
FIGS. 5A and 5B are partial sectional views of the guide heads of the invention showing a conventional microelectrode mounted therein in precise alignment with an oocyte trapped in the well of the perfusion chamber of FIG. 2.
Figure 5B:
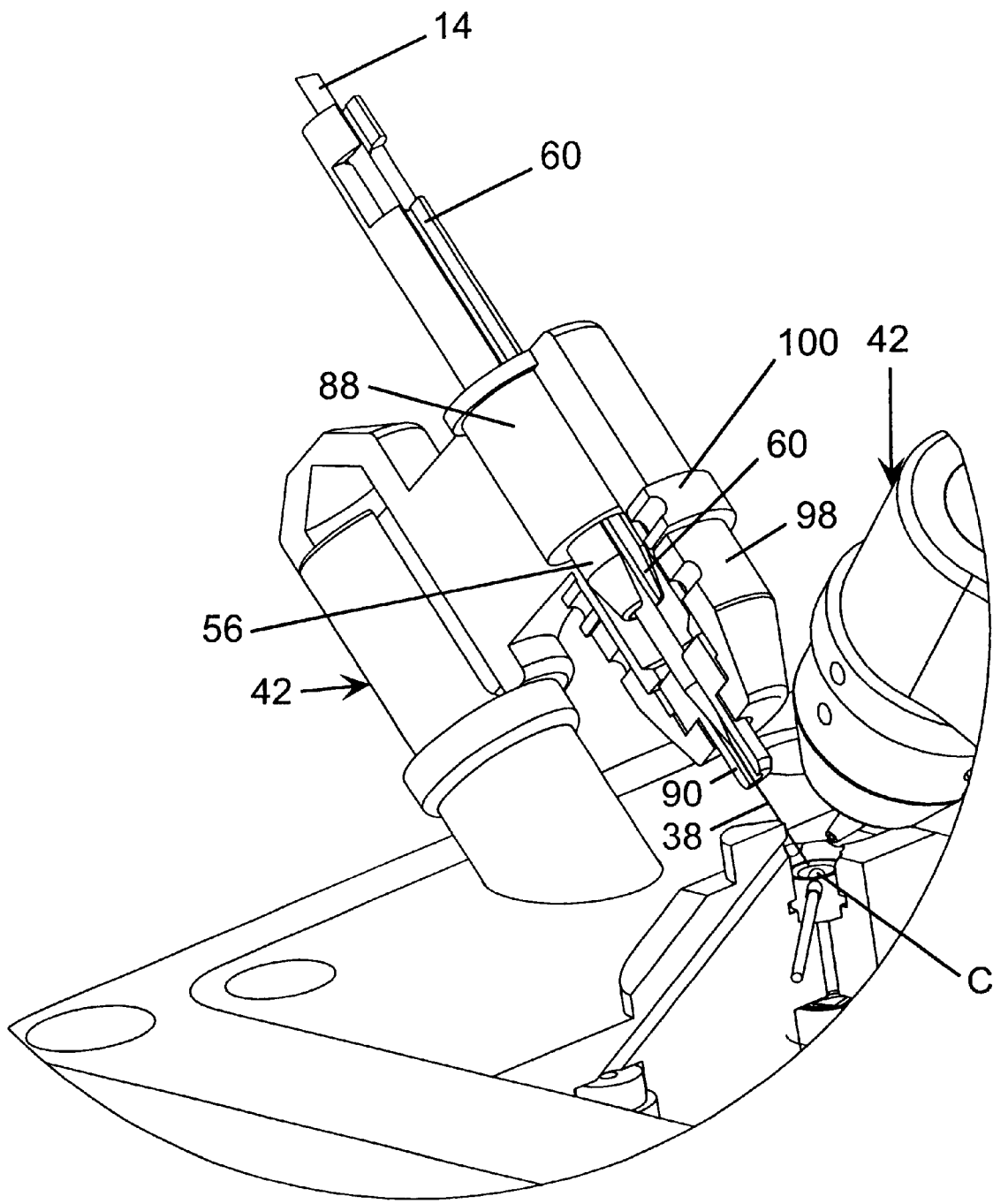

The function of the guide head 42 of the invention is to provide a final and precise alignment of the microelectrode with the oocyte trapped in the perfusion chamber. Accordingly, as shown in FIGS. 5A and 5B, the guide head 42 consists of a structure rigidly connected to the frame 44 of the perfusion chamber and including a perforation 86 longitudinally aligned with the center of a nominal target oocyte in the holding well 32 of the perfusion chamber. A bushing 88 is provided to slidably receive the guide tube 56 at the proximal end of the perforation 86 when the electrode stage 46 is advanced toward the perfusion chamber. In addition, a guide collar 90 is provided to slidably receive and precisely align the microelectrode at the distal end of the perforation 86. The collar 90 consists of a bolt-shaped structure with a longitudinal hole 92 precisely bored to receive in slidable but precise connection the microelectrode of the invention, as illustrated in the figure. Obviously, the connection must be sufficiently loose to permit the axial motion of the electrode, but also sufficiently tight to prevent significant radial shifts of the tip of the electrode as it moves forward in alignment with the target oocyte.

The head 94 of the collar 90 has a flat top surface 96 that overlaps and butts against the distal end of the perforation 86 (see FIG. 5A). Thus, the alignment of the microelectrode retained in the hole 92 can be perfected by varying the radial position of the collar 90 with respect to the axis of the perforation 86. Once such calibration position is established, the collar is pressed in place by an alignment chuck 98 that is threadedly connected to the guide head 42. A threaded lock nut 100 is preferably also used to firmly fix the position of the alignment chuck 98. Therefore, subsequent positioning operations of the same or of a new microelectrode can be conducted without a need to recalibrate the system. This feature is believed to provide a material advantage over prior-art alignment mechanisms.

In order to practice the invention for the purpose of voltage-clamp testing, a perfusion chamber is equipped with the alignment apparatus 40 on two sides of the oocyte, so that both microelectrodes 12 and 14 can be automatically placed within the test cell. In the preferred embodiment of the invention, each electrode is aligned with the center of a nominal 1.0-mm oocyte resting in the perfusion chamber, at a 40-degree angle with respect to the vertical direction (angles $\alpha$ and $\beta$ in FIG. 2). The precise direction of each electrode is calibrated by adjusting the position of the collar 90 within the chuck 98, as detailed above, so that the alignment can be maintained when the microelectrode is replaced. The stage nose 54 is preferably rotatable to a vertical position through an angle of about 140 degrees in order to provide completely unobstructed access to the microelectrode.

Figure 6:
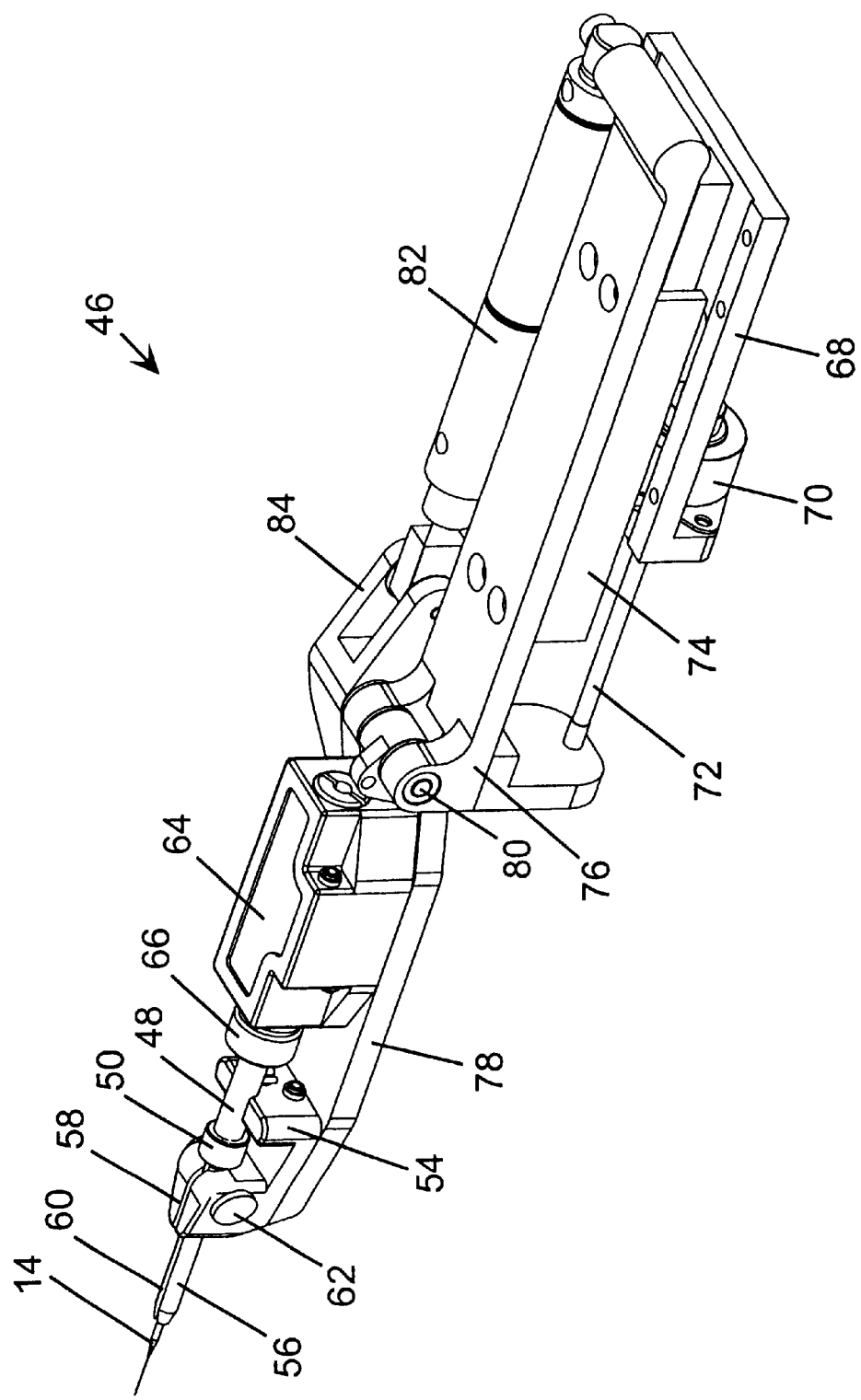
FIG. 6 is an isolated perspective view of the electrode stage of the invention shown in extended position.

In operation, a microelectrode 12 (or 14) is installed by passing it through the longitudinal slots 58,60, inserting its proximal end 52 into the holder 48, and frictionally fastening it in place by tightening the nut 50 (see FIG. 6). Through the action of the ram 82, the stage nose 54 is rotated back to its position aligned with the guide head 42. Then, through the action of the stepper motor 70, the stage nose is advanced toward the guide head, causing the guide tube 56 to be engaged by the bushing 88 and guided toward the collar 90. As the microelectrode advances, it is engaged by the inner bore 92 of the collar 90 and directed precisely toward the oocyte C in the perfusion chamber (see FIG. 5A). The further advancement of the microelectrode is controlled by detecting changes in the impedance and/or voltage measured by the electrode. As those skilled in the art readily understand, a detectible change is observed when the tip of the microelectrode is first immersed in the perfusion solution in the chamber. A second detectible change is measured when the tip of the microelectrode contacts the oocyte, and then again when the tip penetrates the membrane of the oocyte. Accordingly, the advance of the microelectrode can be advantageously controlled using these parameters. For example, the speed of microelectrode advancement may be reduced when the tip of the electrode first contacts the perfusion solution (so as to prevent dimpling and rupturing of the oocyte upon impact); and the forward progress of the electrode may be immediately stopped when the membrane is penetrated. Similarly, in order to further facilitate the penetration of the microelectrode without causing rupture of the oocyte membrane, a high-frequency, mechanical or electrical vibration may be introduced to the tip of the electrode by appropriately controlling the voltage applied to the stepper motor or the electrode, respectively.

While the control of the linear motion of the microelectrode of the invention has been described in terms of measuring impedance and/or voltage and using them as a control parameters, it is clear that it could be accomplished in equivalent feedback manner with optical or other means adapted to detect the position of the electrode's tip with reference to the oocyte's membrane. The final stages of advancement could also be controlled by feedforward control means by limiting the progress of the electrode to a predetermined distance after immersion of the microelectrode in the perfusion solution, such distance having been determined empirically to ensure penetration through the membrane of an average-size oocyte. In all such cases, the apparatus of the invention is suitable for automated computer control using conventional detection and actuation apparatus.

Figure 7:
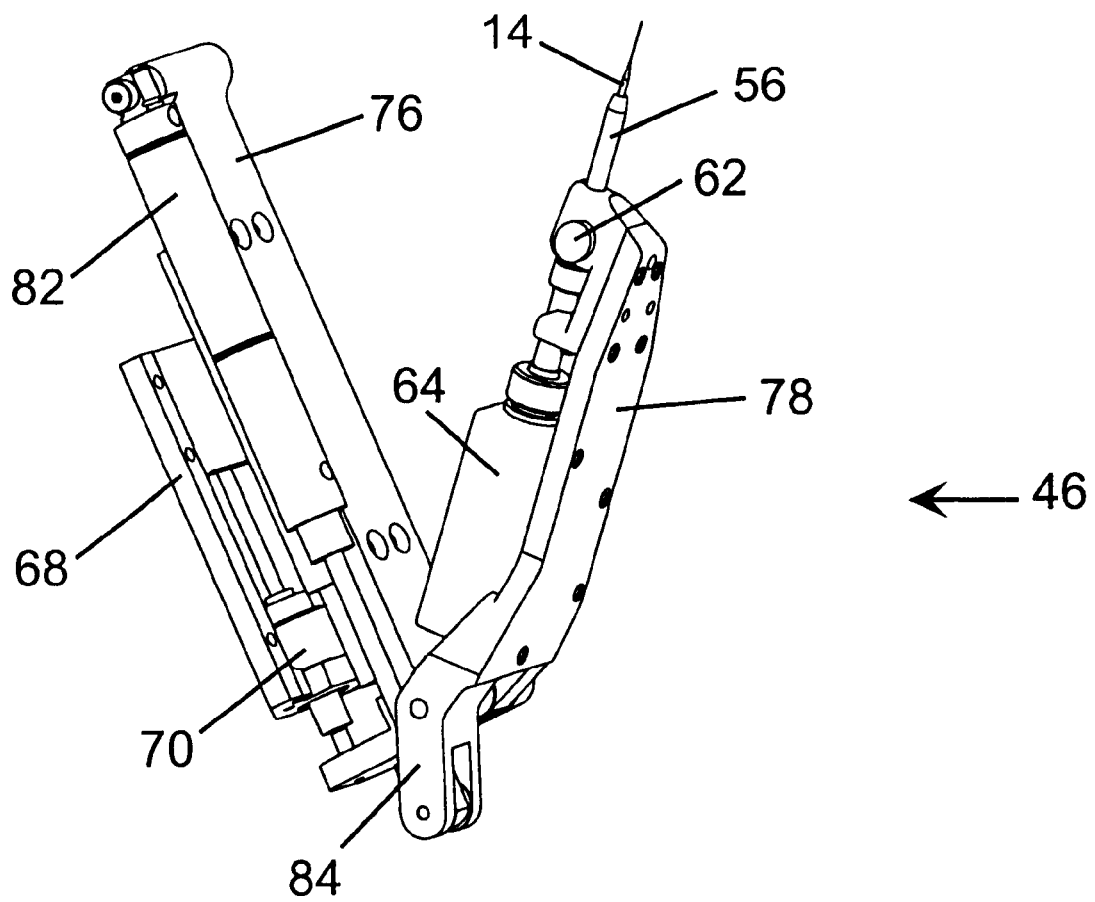
FIG. 7 is an isolated perspective view of the electrode stage of the invention shown in rotated position.
Figure 7:
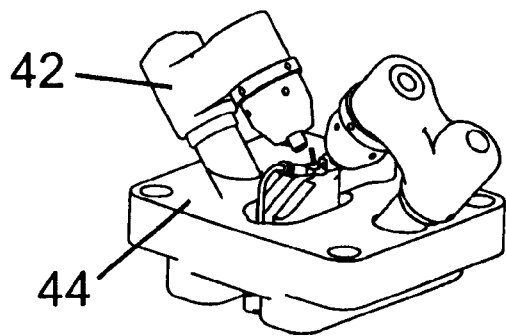

In order to replace the microelectrode 12 (or 14), the stepper motor is actuated to retract the electrode stage 46 so that the electrode is completely out of the guide head 42. In the preferred embodiment of the invention, that is accomplished with a linear-motion range of about 50 mm. When the microelectrode is fully retracted, the hydraulic cylinder 82 is automatically actuated to rotate the guide head 42 upwards to a predetermined desired position, as illustrated in FIG. 7. The microelectrode is then released by loosening the nut 50 and is removed from the holder 48, preferably through the slots 58 and 60 in the stage nose 54 and guide tube 56, respectively. A new microelectrode can then be installed as described above. It is noted that the removal and installation of microelectrodes are the only manual operations required with the apparatus of the invention, except for replacing oocytes.

Figure 8:
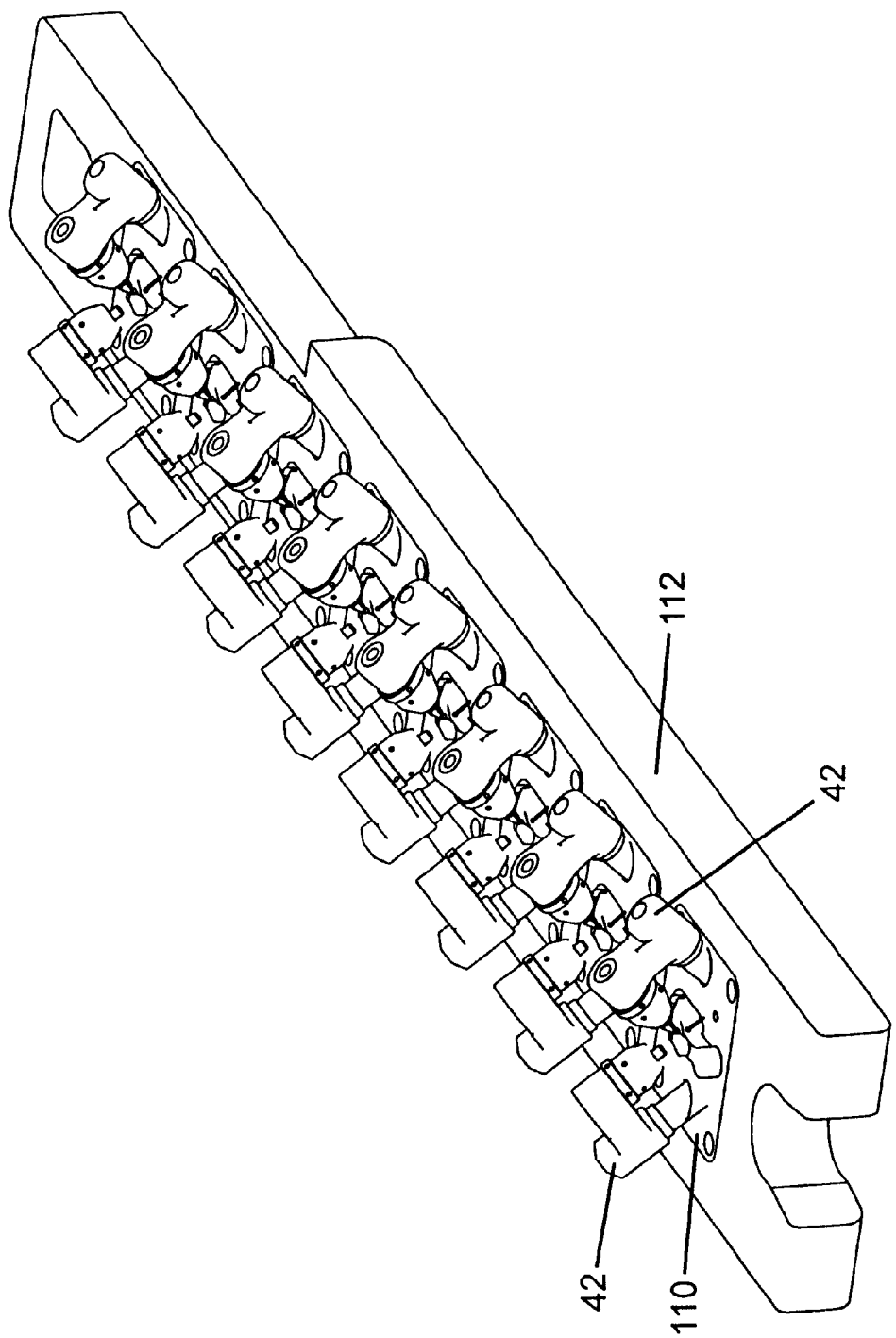
FIG. 8 is a perspective view a modular, eight-unit perfusion-chamber tray, including a set of guide heads rigidly mounted on each chamber, for carrying out multiple, sequential experiments in parallel.
Figure 9:
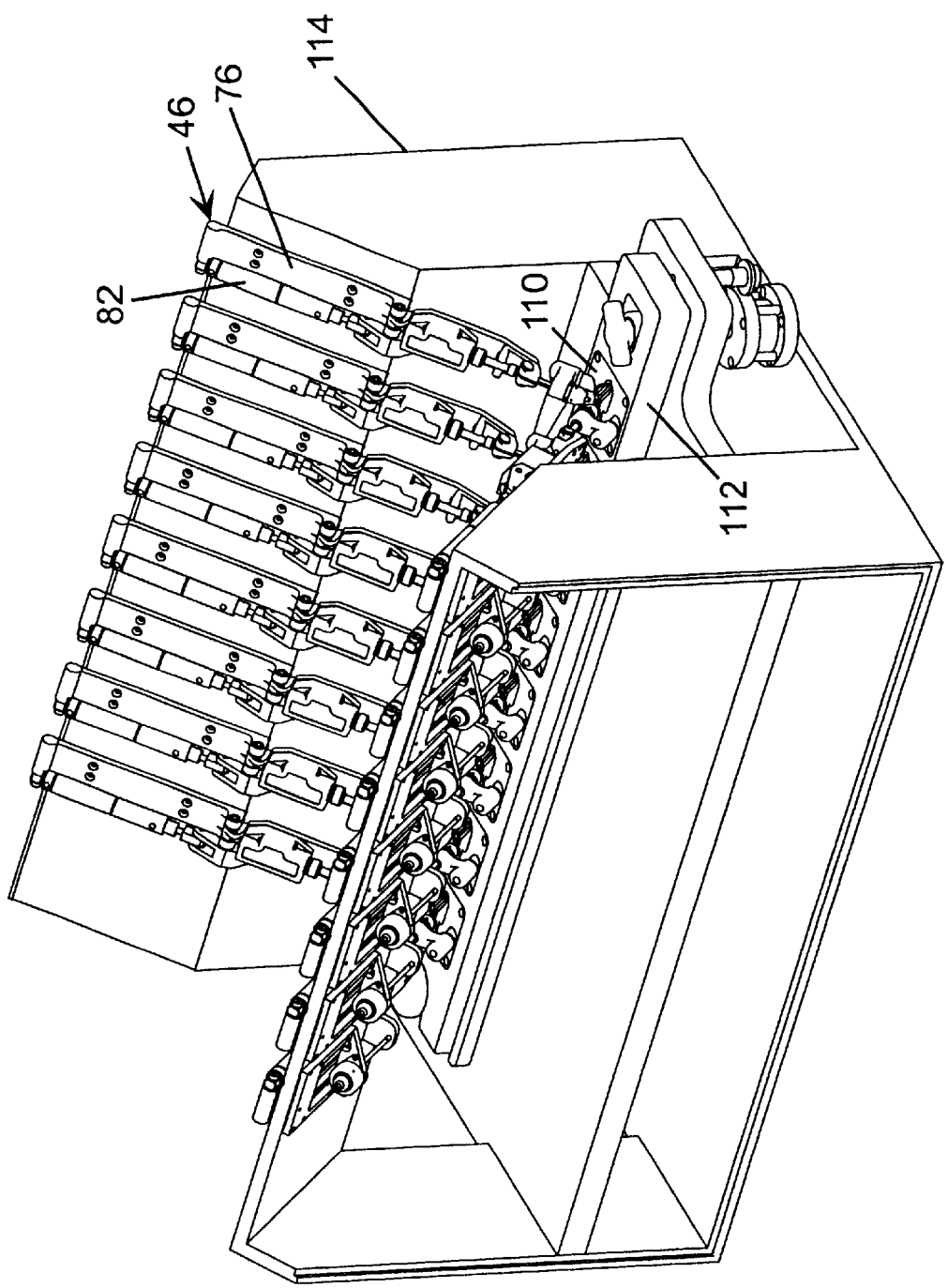
FIG. 9 shows the tray of FIG. 8 mounted in a frame that rigidly connects the perfusion-chamber modules to corresponding electrode stages adapted to function in cooperation with the guide heads shown in that figure, so that each perfusion chamber can be operated independently to perform sequential measurements using multiple perfusion solutions.

Because of the suitability of the invention for automated implementation, it can be used with batteries of perfusion chambers operated in parallel to increase efficiency and productivity. FIGS. 8 and 9 illustrate such an implementation with eight perfusion-chamber modules 110 mounted on a single support tray 112. Each module 110 includes guide heads 42 in fixed aligned position with respect to the perfusion chamber. The tray 112 is installed in a frame 114 that rigidly connects the modules 110 to corresponding electrode stages 46 adapted to function as described. Accordingly, each perfusion chamber can be operated independently to perform sequential measurements using multiple perfusion solutions, as known in the art.

Figure 10:
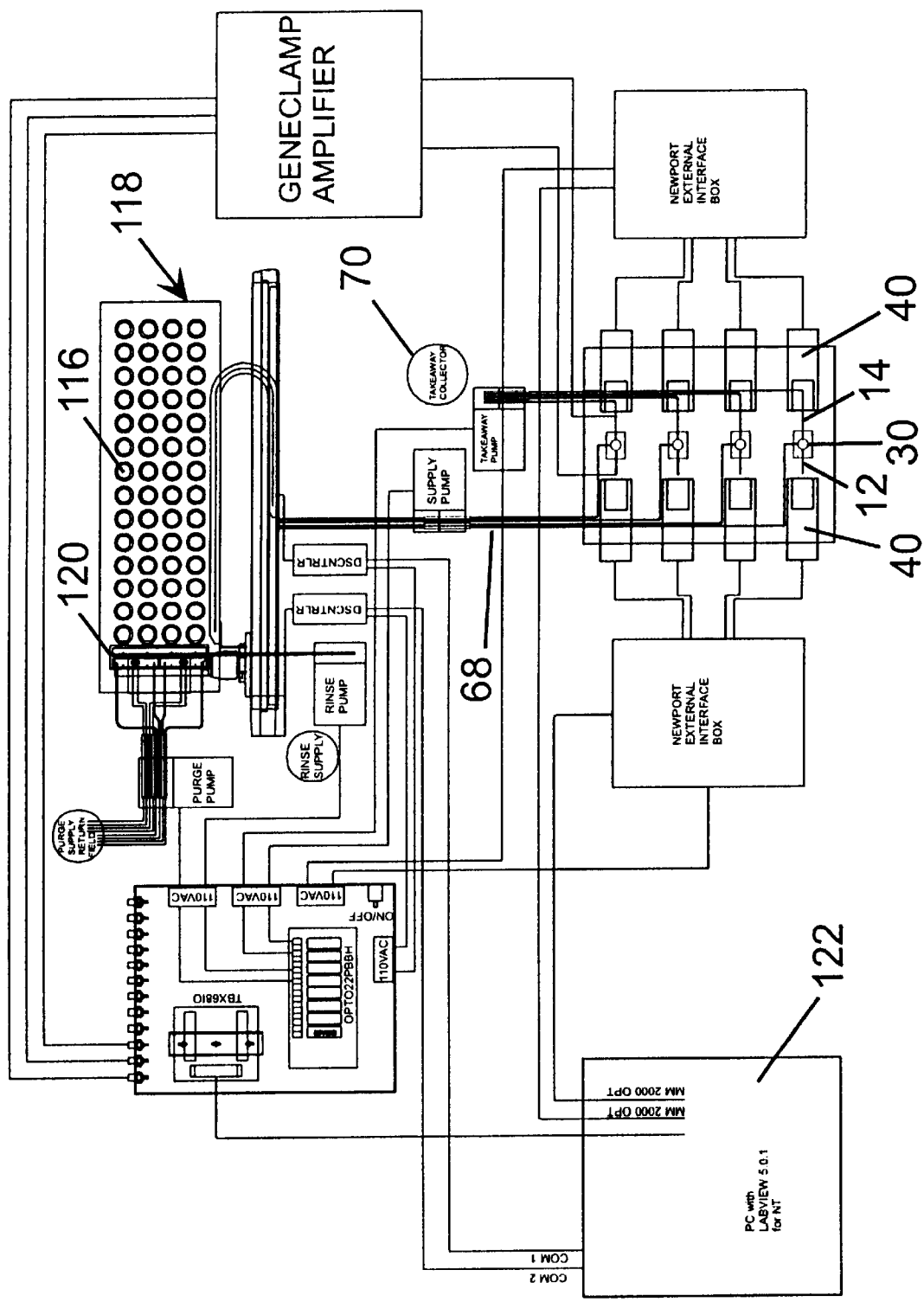
FIG. 10 is a schematic diagram of the apparatus, including fluid piping and electronic hardware, used to operate the system of FIG. 9 in automated fashion.

FIG. 10 illustrates schematically the automated operation of a bank of four perfusion chambers mounted in a row within corresponding sets of microelectrode pairs aligned according to the invention. Test fluids, to be independently applied to the oocytes placed in the chambers, are pumped from separate vials 116 arranged in an array 118. The supply tubing can be connected to any given vial using a "pick and place" two-dimensional robotic positioner 120 under control of a computer 122. The positioner has a sufficient range to reach and apply multiple different solutions during an experiment. In the preferred embodiment of the invention, the vials 116 are chosen to hold a sufficient volume of solution (about 20 ml) to permit up to 5 minutes of application at a rate of 4 ml/min (a maximum desirable flow rate for oocyte recordings).

Figure 11:
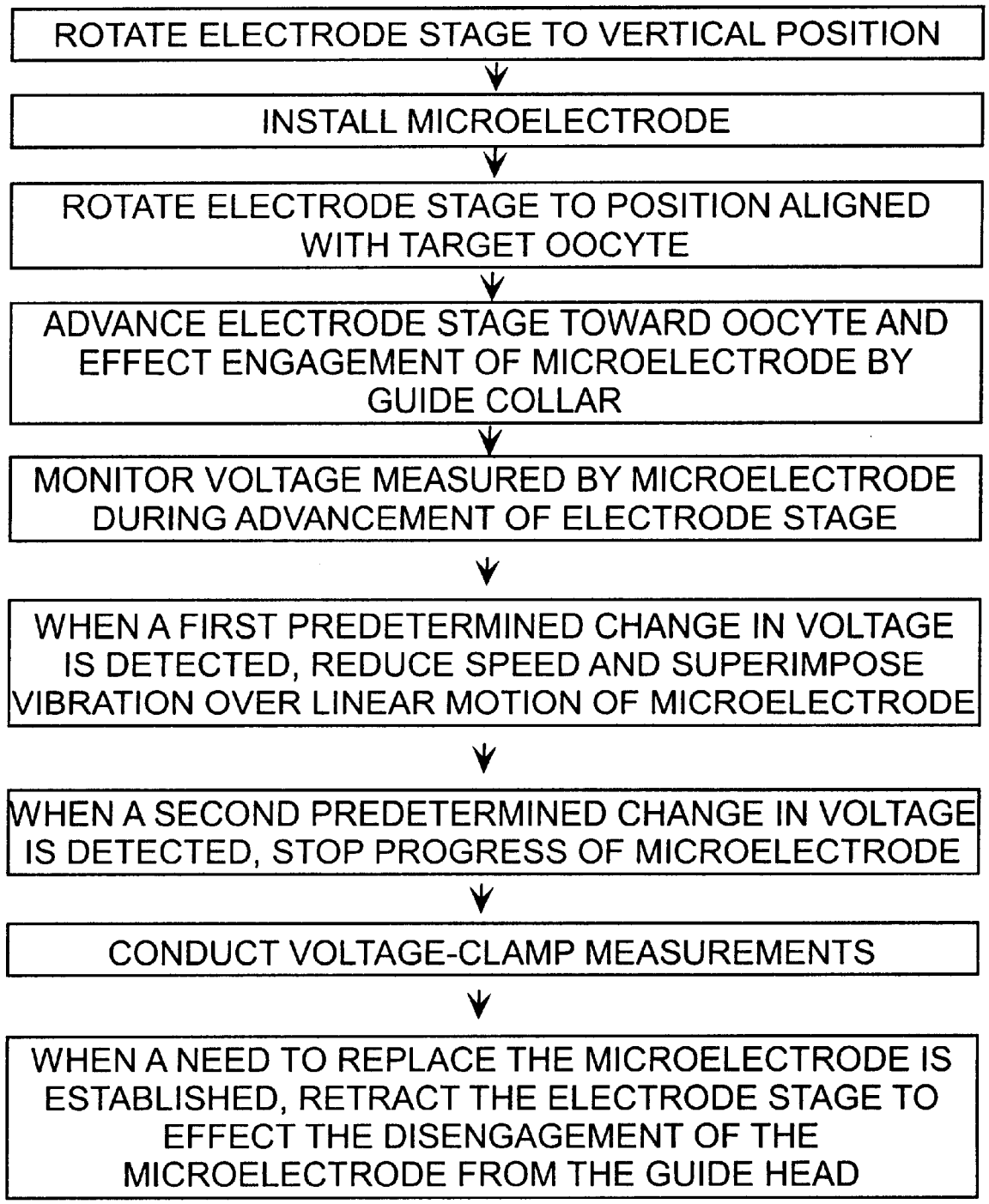
FIG. 11 is a flow chart illustrating the sequence followed for automatically positioning the voltage-clamp electrodes into the oocytes.

The voltage-clamp system is controlled with the alignment apparatus of the invention. Based on the precise geometry of the chambers, the electrodes are initially positioned automatically within less than about 100 $\mu$m of the oocyte's membrane and then advanced until a voltage change of at least about 10 mV in the recorded voltage indicates cell penetration. Oocytes are typically about 0.8–1.2 mm in diameter and penetration normally occurs within about 400 $\mu$m of first contact with a microelectrode. Therefore, this distance can be advantageously used for quick, automated application as a result of the reproducible placement of the oocytes within the perfusion chamber, as afforded, for example, by the invention disclosed in Ser. No. 09/586,633. FIG. 11 illustrates in flow-chart form the sequence followed for automatically positioning the voltage-clamp electrodes into the oocytes. Thus, it has been demonstrated that the alignment mechanism of the invention is suitable for automating the parallel, higher-throughput, recording process of oocyte electrophysiology experiments. The invention made it possible to automate the electrode alignment and penetration into the oocyte within a system of automated fluid delivery to the chambers. It is noted that the open top and the surface configuration of the support structure disclosed in Ser. No. 09/586,633 are particularly suitable for the alignment apparatus of the invention, as well as for combining preparatory microinjection and electrophysiological recording of oocytes in the same chamber. A further desirable objective remains the automation of oocyte delivery and preparation in the perfusion chamber, which would provide additional efficiency to the process of voltage-clamp testing.

Various changes in the details, steps and components that have been described may be made by those skilled in the art within the principles and scope of the invention herein illustrated and defined in the appended claims. For example, the invention has been described in terms of a particular perfusion chamber and oocytes, but the same inventive principles would apply for any other type of chamber or other sample material that can be advantageously held in a chamber well. Therefore, while the present invention has been shown and described herein in what is believed to be the most practical and preferred embodiments, it is recognized that departures can be made therefrom within the scope of the invention, which is not to be limited to the details disclosed herein but is to be accorded the full scope of the claims so as to embrace any and all equivalent apparatus and procedures.

We claim:

1. A two-electrode voltage-clamp apparatus for performing electrophysiology recording on a test sample placed in a perfusion chamber, comprising:
   a) a perfusion chamber for holding a test sample; and
   b) a pair of electrode alignment mechanisms directed toward the perfusion chamber, wherein each mechanism includes:
      a guide head fixedly and rigidly connected to the perfusion chamber; and
      an electrode stage anchored in fixed spatial relation with respect to the guide head;
      wherein the electrode stage includes a means for holding a microelectrode; and the guide head includes a means for precisely aligning said holding means and the microelectrode with the test sample.

2. The apparatus of claim 1, wherein the holding means is movable between a first position aligned with said alignment means and a second position adapted to provide access to said microelectrode.

3. The apparatus of claim 1, wherein the electrode stage further includes a mechanical means for effecting the engagement of the holding means with the aligning means while the holding means is in said first position.

4. The apparatus of claim 1, wherein said means for precisely aligning the holding means and the microelectrode with the test sample includes a guide collar adapted to slidably receive and precisely align the microelectrode with the test sample.

5. The apparatus of claim 4, wherein said guide collar is radially movable within the guide head to perfect the alignment of the microelectrode retained therein, and wherein said guide collar is fixed in a perfected alignment position by a chuck threadedly connected to the guide head.

6. The apparatus of claim 1, wherein said means for holding the microelectrode includes a tubular holder and a threaded nut adapted to frictionally retain the microelectrode within the holder.

7. The apparatus of claim 3, wherein said means for effecting the engagement of the holding means with the aligning means includes a first actuator adapted to move the holding means between said first and second positions and a second actuator adapted to reversibly advance the holding means and the microelectrode for engagement with said means for precisely aligning the holding means and the microelectrode with the test sample.

8. The apparatus of claim 7, wherein said first actuator comprises a hydraulic cylinder acting on a lever arm of a hinged plate containing the holding means, said cylinder being operable between said first and second positions of the holding means.

9. The apparatus of claim 7, wherein said first actuator comprises a stepper motor acting on a lever arm of a hinged plate containing the holding means, said stepper motor being operable between said first and second positions of the holding means.

10. The apparatus of claim 7, wherein said second actuator comprises a screw drive acting on a slidable plate containing the holding means, said screw drive being operable between an extended position where the holding means and the microelectrode are fully engaged by said aligning means and a retracted position where the holding means and the microelectrode are fully disengaged from the guide head.

11. The apparatus of claim 1, wherein said test sample is an oocyte.

12. The apparatus of claim 1, wherein said perfusion chamber includes a support structure having a sloped top surface progressively converging downward toward a holding well.

13. The apparatus of claim 12, wherein said holding well has a bottom surface conforming to a geometry of an oocyte.

14. The apparatus of claim 3, further comprising control means for automatically effecting the engagement of the holding means and the microelectrode with said aligning means.

15. The apparatus of claim 1, further comprising means for detecting a contact between said microelectrode and a perfusion solution in the perfusion chamber.

16. The apparatus of claim 15, further comprising means for advancing the microelectrode by a predetermined distance toward the test sample after detection of said contact between the microelectrode and the perfusion solution in the perfusion chamber.

17. The apparatus of claim 16, further comprising means for vibrating said microelectrode after detection of said contact between the microelectrode and the perfusion solution in the perfusion chamber.

18. The apparatus of claim 15, further comprising means for vibrating said microelectrode after detection of said contact between the microelectrode and the perfusion solution in the perfusion chamber.

19. The apparatus of claim 1, further comprising means for detecting a penetration of said microelectrode through a membrane of said test sample.

20. The apparatus of claim 1, wherein the holding means is movable between a first position aligned with said alignment means and a second position adapted to provide access to said microelectrode; the electrode stage further includes a mechanical means for effecting the engagement of the holding means with the aligning means while the holding means is in said first position; said test sample is an oocyte; said perfusion chamber includes a support structure having a sloped top surface progressively converging downward toward a holding well with a bottom surface conforming to a geometry of the oocyte; said means for precisely aligning the holding means and the microelectrode with the oocyte includes a guide collar adapted to slidably receive and precisely align the microelectrode with the oocyte; said guide collar is radially movable within the guide head to perfect the alignment of the microelectrode retained therein, and the guide collar is fixed in a perfected alignment position by a chuck threadedly connected to the guide head; said means for holding the microelectrode includes a tubular holder and a threaded nut adapted to frictionally retain the microelectrode within the holder; said means for effecting the engagement of the holding means with said aligning means includes a first actuator adapted to move the holding means between said first and second position and a second actuator adapted to reversibly advance the holding means and the microelectrode for engagement with said aligning means; said first actuator comprises a hydraulic cylinder acting on a lever arm of a linearly slidable and rotatably hinged plate containing the microelectrode, said cylinder being operable between a first angular position where the microelectrode is aligned with the guide head and a second angular position selected to provide access to the microelectrode; and said second actuator comprises a screw drive acting on a slidable plate containing the holding means, said screw drive being operable between an extended position where the holding means and the microelectrode are fully engaged by said aligning means and a retracted position where the holding means and the microelectrode are fully disengaged from the guide head.

21. Apparatus for performing multiple electrophysiology recording measurements in parallel with multiple perfusion chambers, wherein each chamber includes a guide head and an electrode stage as described in claim 1.

22. Apparatus for aligning a microelectrode with a test sample placed in a perfusion chamber of an electrophysiology recording device, comprising:
a guide head fixedly and rigidly connected to a support for the perfusion chamber; and
an electrode stage anchored in fixed spatial relation with respect to the guide head;
wherein the electrode stage includes a means for holding the microelectrode; the guide head includes a means for precisely aligning said holding means and the microelectrode with the test sample; the holding means is movable between a first position aligned with said alignment means and a second position adapted to provide access to said microelectrode; and the electrode stage further includes a mechanical means for effecting the engagement of the holding means with the aligning means while the holding means is in said first position.

23. The apparatus of claim 22, wherein said means for precisely aligning the holding means and the microelectrode with the test sample includes a guide collar adapted to slidably receive and precisely align the microelectrode with the test sample.

24. The apparatus of claim 23, wherein said guide collar is radially movable within the guide head to perfect the alignment of the microelectrode retained therein, and wherein said guide collar is fixed in a perfected alignment position by a chuck threadedly connected to the guide head.

25. The apparatus of claim 22, wherein said means for effecting the engagement of the holding means with the aligning means includes a first actuator adapted to move the holding means between said first and second positions and a second actuator adapted to reversibly advance the holding means and the microelectrode for engagement with said means for precisely aligning the holding means and the microelectrode with the test sample.

26. The apparatus of claim 22, wherein said test sample is an oocyte.

27. The apparatus of claim 22, further comprising control means for automatically effecting the engagement of the holding means and the microelectrode with said aligning means.

28. The apparatus of claim 22, further comprising means for detecting a contact between said microelectrode and a perfusion solution in the perfusion chamber.

29. The apparatus of claim 22, further comprising means for detecting a penetration of said microelectrode through a membrane of said test sample.

30. Apparatus for performing multiple electrophysiology recording measurements in parallel with multiple perfusion chambers, wherein each chamber includes a pair of guide heads and a corresponding pair of electrode stages as described in claim 22.

31. A method for aligning a microelectrode with a test sample placed in a perfusion chamber of an electrophysiology recording device, comprising the following steps:

(a) providing a guide head fixedly and rigidly connected to the perfusion chamber;

(b) providing an electrode stage anchored in fixed spatial relation with respect to the guide head; wherein the electrode stage includes a means for holding the microelectrode, the guide head includes a means for precisely aligning said holding means and the microelectrode with the test sample, the holding means is movable between a first position aligned with said alignment means and a second position adapted to provide access to said microelectrode, and the electrode stage further includes a means for effecting the engagement of the holding means with the aligning means while the holding means is in said first position; and (c) effecting the engagement of holding means with said aligning means.

32. The method of claim 31, wherein said means for precisely aligning the holding means and the microelectrode with the test sample includes a guide collar adapted to slidably receive and precisely align the microelectrode with the test sample.

33. The method of claim 32, wherein said guide collar is radially movable within the guide head to perfect the alignment of the microelectrode retained therein, and wherein said guide collar is fixed in a perfected alignment position by a chuck threadedly connected to the guide head.

34. The method of claim 31, wherein said means for holding the microelectrode includes a tubular holder and a threaded nut adapted to frictionally retain the microelectrode within the holder.

35. The method of claim 31, wherein said step (c) of effecting the engagement of the holding means with said alignment means is carried out with a linear actuator adapted to reversibly advance the holding means to become engaged by said alignment means.

36. The method of claim 35, wherein said linear actuator comprises a screw drive acting on a slidable plate containing the microelectrode, said screw drive being operable between an extended position where the microelectrode is fully engaged by said alignment means and a retracted position where the microelectrode is fully disengaged from the guide head.

37. The method of claim 31, further comprising the step of providing an angular actuator adapted to align the microelectrode with the guide head, said angular actuator being operable between a first position where the microelectrode is aligned with the guide head and a second position selected to provide access to the microelectrode; and the step of placing the microelectrode in said second position for removing the microelectrode and for installing a replacement microelectrode.

38. A method of conducting sequential voltage-clamp measurements with electrophysiology apparatus including a perfusion chamber adapted to receive a test sample, a guide head fixedly and rigidly connected to the perfusion chamber, means in the guide head for precisely aligning the microelectrode with the test sample, an electrode stage disposed in fixed spatial relation with respect to the guide head, means for holding the microelectrode in the electrode stage, and mechanical means for effecting the engagement of the microelectrode with the means for precisely aligning the microelectrode with the test sample, said method comprising the following steps:

(a) installing a microelectrode in said holding means in the electrode stage;

(b) effecting the engagement of the microelectrode with said means for precisely aligning the microelectrode with the test sample;

(c) advancing the microelectrode toward said test sample;

(d) interrupting step (c) when the microelectrode penetrates a membrane of the test sample;

(e) carrying out voltage-clamp measurements according to a predetermined sequential schedule;

(f) disengaging the microelectrode from said means for precisely aligning the microelectrode with the test sample;

(g) replacing the microelectrode with a new microelectrode; and (h) sequentially repeating steps (b) through (g) with the new microelectrode.

39. The method of claim 38, wherein steps (b) through (f) are carried out automatically under computer control.

40. The method of claim 38, further comprising the step of detecting a contact between said microelectrode and a perfusion solution in the perfusion chamber during step (c).

41. The method of claim 40, further comprising the step of advancing the microelectrode by a predetermined distance toward the test sample after detection of said contact between the microelectrode and the perfusion solution in the perfusion chamber.

42. The method of claim 40, further comprising the step of vibrating said microelectrode after detecting said contact between the microelectrode and the perfusion solution in the perfusion chamber.

43. The method of claim 41, further comprising the step of vibrating said microelectrode after detecting said contact between the microelectrode and the perfusion solution in the perfusion chamber.

44. The method of claim 38, wherein step (d) is carried out by detecting a change in a voltage measured by the microelectrode.

45. The method of claim 37, wherein the test sample is an oocyte cell.

* * * * *